United States Patent [19]

Hippel et al.

[11] Patent Number: 5,658,844
[45] Date of Patent: Aug. 19, 1997

[54] CATALYST FOR THE PRODUCTION OF CYANOPYRICLINES

[75] Inventors: Lukas V. Hippel, Alzenau; Armin Neher, Wesseling; Dietrich Arntz, Oberursel, all of Germany

[73] Assignee: Degussa Aktiengesellschaft, Frankfurt am Main, Germany

[21] Appl. No.: 595,253

[22] Filed: Feb. 1, 1996

[30] Foreign Application Priority Data

Feb. 9, 1995 [DE] Germany .................. 195 04 283.2

[51] Int. Cl.$^6$ .................................................. B01J 23/16
[52] U.S. Cl. ..................... 502/353; 502/344; 502/243; 502/246; 502/247; 502/249
[58] Field of Search .......................... 502/353, 344, 502/243, 246, 247, 249

[56] References Cited

U.S. PATENT DOCUMENTS

| | | | |
|---|---|---|---|
| 4,447,612 | 5/1984 | Beschke et al. | 546/286 |
| 4,482,719 | 11/1984 | Helmut et al. | 546/286 |
| 4,508,848 | 4/1985 | Dolhyj et al. | 502/239 |
| 4,814,478 | 3/1989 | Glaeser et al. | 558/319 |
| 5,432,141 | 7/1995 | Brazdil, Jr. et al. | 502/311 |

FOREIGN PATENT DOCUMENTS

| | | |
|---|---|---|
| 0 055 534 | 7/1982 | European Pat. Off. . |
| 0 509 414 | 9/1982 | European Pat. Off. . |
| 95/05895 | 3/1995 | WIPO . |

OTHER PUBLICATIONS

Database WPI, Section Ch, Week 8840, Derwent Publications, JP 63-208,575, Aug. 1988.

*Primary Examiner*—Glenn A. Caldarola
*Assistant Examiner*—Nadine Preisch
*Attorney, Agent, or Firm*—Beveridge, DeGrandi, Weilacher & Young, LLP

[57] ABSTRACT

A method of producing cyanopyridines by means of the catalytic reaction of methylpyridines with ammonia and oxygen at elevated temperature using catalysts consisting of compounds of the elements antimony, vanadium, silicon, titanium and oxygen and compounds of one or more of the alkali metals as well as a method of producing the catalysts and the catalysts themselves.

34 Claims, No Drawings

CATALYST FOR THE PRODUCTION OF CYANOPYRICLINES

INTRODUCTION AND BACKGROUND

The present invention relates to a method of producing cyanopyridines by means of the catalytic reaction of methylpyridines with ammonia and oxygen at elevated temperature. The present invention also relates to catalysts suitable for this purpose which contain compounds of the elements antimony, vanadium, silicon, titanium and oxygen and compounds of one or more of the alkali metals. Furthermore, the present invention relates to the method of producing the catalysts and method of their use.

Several methods of producing cyanopyridines by reacting the appropriate methylpyridines with oxygen and ammonia at elevated temperature in the gaseous phase are known. They differ from each other by the reaction conditions and especially by the catalyst composition. Of the known methods and catalysts, the significant ones are those for use on an industrial scale which have a good selectivity and dwell time and which at the same time have a high space-time yield.

It is furthermore known that catalysts can be used which are produced by pretreating mixtures containing antimony and vanadium in an atomic ratio of 1.1:1 to 50:1 and at least one of the elements iron, copper, titanium, cobalt, manganese and nickel and optionally a carrier substance by heating to temperatures of 600° to 1100° C. in the presence of oxygen (U.S. Pat. No. 3,927,007 which is incorporated by reference in its entirety, especially for its teaching of compounds of Sb, V and Ti which can be used to form a catalyst; DE 20 39 497). This method achieves high space-time yields but the selectivity is unsatisfactory.

It is also known that catalysts for the ammonoxidation of methylpyridines based on titanium oxide/silicon oxide carriers can be produced which are covered with the oxides of antimony and of vanadium (U.S. Pat. No. 4,939,260 which is incorporated by reference in its entirety; EP 0,290,996 B1). These catalysts have yields of only around 85% in the case of the ammonoxidation of 3-methylpyridine.

It is furthermore known that catalysts for the production of 3-cyanopyridine with good selectivity and high space-time yield can be produced from layer-lattice silicates, highly dispersed silicon oxide and oxygen compounds of the elements antimony and vanadium and from at least one of the elements iron, copper, titanium, cobalt, manganese and nickel (EP 0,059,414 B1; U.S. Pat. No. 4,447,612 which is incorporated by reference in its entirety). The production of these catalysts is very expensive and requires, among other things, an intermediate calcining with subsequent grinding.

SUMMARY OF THE INVENTION

One object of the present invention is to provide catalysts whose production is comparatively simple and which achieve high selectivities in combination with high space-time yields at high conversions. Catalysts for the conversion of methylpyridines with ammonia and oxygen to the corresponding cyanopyridines have now been found which correspond to the general empirical formula $$Sb_a V_b Ti_c X_d^1 X_e^2 O_f$$

in which $X^1$ signifies silicon, which Si stems from the highly dispersed silica introduced during the catalyst production and from at least one layer-lattice silicate, and $X^2$ signifies at least one of the elements of the alkali series (Li, Na, K, Rb, Cs), a=3–10,
b=0.5–2,
c=3–10,
d=2–20,
e=0.01–2,
f=atom number necessary for the stoichiometric saturation of the remaining components based on the valencies and constituents.

Another object of the present invention is to provide a method of producing such catalysts. In order to produce the catalysts in accordance with the present invention, antimony, vanadium, and titanium, as well as the elements silicon and the elements of the alkali series, are used, advantageously as compounds with oxygen, in elementary form or in the form of compounds which can be readily converted into oxygen compounds such as e.g. nitrates, oxalates, or carbonates; see column 2, line 43-column 3, line 2 of U.S. Pat. No. 3,927,007 and column 2, lines 14–21 of U.S. Pat. No. 4,447,612 for examples thereof. One or more of these substances optionally as a solution or slurry in water, are then introduced. The solution with solid constituents obtained in this manner is boiled with agitation and maintained at first at a low pH between 0 and 2, preferably 0.5 and 1.5.

Toward the end of this boiling phase the reaction mixture is cooled off, the pH raised with a base, preferably ammonia, and adjusted to a value between 3 and 6, preferably between 4 and 5, and re-boiled. The suspension obtained in this manner can be directly processed further after cooling off to <50° C. For this, it is dried in a spray dryer at temperatures between 200° and 700° C. at revolutions between 20,000 and 60,000 rpms. The particle size can be purposefully adjusted as a function of the temperature and the speed of rotation. The separation of the powder takes place in a cyclone. The powder obtained in this manner can be directly processed further as set forth hereinafter. In comparison to the state of the art, the expensive drying, grinding and intermediate calcining are eliminated in this manner.

DETAILED DESCRIPTION OF THE INVENTION

According to a preferred embodiment of the invention, the catalysts preferably have a BET surface area (Brunauer, Emmett, and Tellet's surface area determination) of 5 to 50 $m^2/g$, a total pore volume of 0.1 to 1 ml/g and an average pore radius of 1 to $15 \times 10^{-8}$ m. They bring about a high conversion with very good selectivities with high space-time yields and processing times. Catalysts containing antimony, vanadium, titanium, silicon and potassium are especially advantageous.

According to a more detailed aspect of the method of preparing the catalyst, for preparing an extrusion of the catalyst product customary extrusion aids and pore formers; e.g. ammonium carbonate, carbohydrates, starch, cellulose, or polyvalent alcohols and solvents, are added to the powder obtained in the manner previously described. A pasty mass results by intimate kneading which is extruded in an extruder (e.g., a conventional screw-type extrusion machine) through a nozzle. The length of the extrudate is a function of the rate of extrusion and the diameter of the extrusion equipment. The addition of extrusion aids and pore formers without solvent to the processed amount of catalyst is 1 to 30% by weight, preferably 5 to 20% by weight. Suitable solvents are in particular water, organic solvents miscible with water, especially mono- and polyvalent alcohols such as methanol, glycerol or glycol as well as mixtures of these liquids.

The ratios of quantities of substances are preferably selected so that the atomic ratio of titanium to vanadium in the catalysts is between 2:1 and 8:1. The atomic ratios of antimony to vanadium are advantageously between 2:1 and 20:1, preferably between 2:1 and 10:1. The silicon portion is composed of highly dispersed silica with a BET surface area of 50 to 500 m$^2$/g, preferably of 100 to 300 m$^2$/g, and a thermally pretreated layer-lattice silicate, preferably montmorillonite with a BET surface area of 0.1 to 10 m$^2$/g. The weight ratio of highly dispersed silica to layer-lattice silicate is 1:1 to 1:10, preferably 1:1 to 1:5. The atomic amount of silicon based on all the metals is 20 to 70%, preferably 30 to 50%. The ratio of all metals to that of the alkali metals used is between 20:0.01 and 20:5, preferably between 20:0.1 and 20:3.

Naturally occurring layer-lattice silicate generally requires a pretreatment for use in accordance with the present invention. It is finely powdered and heated, advantageously under constant movement, e.g. in a rotary kiln or fluid-bed kiln, to temperatures between 900° and 1200° C. The heating time is a function of the type of layer-lattice silicate, of the temperature, and of the oven type. In most instances the substance is maintained at temperatures in the cited range for at least one hour but not longer than 10 hours. It is preferable to use montmorillonite as layer-lattice silicate and a treatment time of 4 to 6 hours at 975° to 1100° C.

The highly dispersed silicon dioxide can be obtained in various ways, e.g. by pyrolysis of silicon compounds (e.g., silicon tetrachloride, trichlorosilane) or by precipitation from solutions of silicon compounds (e.g., sodium silicate). It advantageously has a BET surface area of approximately 50 to 500 m$^2$/g, preferably of 100 to 300 m$^2$/g.

In order to produce the catalysts of the invention, the initial substances are intimately mixed in a form which is distributed as finely as possible. It has proven to be advantageous to thereby add water and, if necessary, organic solvents miscible with water, especially mono- and polyvalent alcohols such as methanol, glycerol or glycol, as well as mixtures of these liquids. Preferred methods of operation for the preparation of the catalysts include to first place antimony or antimony trioxide under agitation into water and treat it with nitric acid at boiling temperature and then to add the other elements as nitrates or ammonium salts of their oxo acids, the titanium preferably as finely divided titanium dioxide, the silicon as silica, and the layer-lattice silicate preferably as montmorillonite.

Another preferred method is to first receive all elements in the form of their oxides, ammonium salts of their oxygen acids or nitrates under agitation in water and to add nitric acid last; see column 2, line 43-column 3, line 2 of U.S. Pat. No. 3,927,007 and column 2, lines 14–21 of U.S. Pat. No. 4,447,612 for examples of oxygenated compounds. The batch is then boiled under agitation and reflux. After the boiling phase the acid is neutralized with NH$_3$ under further agitation and the product produced in this manner is transferred via a solids separator into a spray dryer. The spray dryer is preferably operated with a flow rate of 1 to 2 m/sec, measured in the introduction charging pipe, with an air inlet temperature of 400° to 700° C. at an atomizer rotation speed of 20,000 to 60,000 rpm. The particle obtained in this manner has a particle size of 1 to 5×10$^{-5}$ m and a BET surface area of 80 to 120 m$^2$/g.

Forming and extrusion aids as well as a solvent or solvent mixture are added to the catalyst for formation and extrusion and a mass capable of extrusion is obtained by kneading. This mass is extruded in such a manner that formed materials are obtained with a length of at least 3 and a maximum of 10 mm. Extrusion presses, screw-type extrusion machines or two-shaft extruders are especially suitable for this purpose. The accumulating briquets are dried (temperature 20° to 200° C.) and then tempered in the presence of oxygen without further intermediate treatment.

Rotary kilns and muffle ovens have proved to be especially suitable for tempering. A final tempering between 300° and 800° C., preferably between 550° and 750° C., leads to the most active and most selective catalysts. This avoids the expensive temperature process of the state of the art (EP-B 0.059.414).

The finished catalyst products of the invention generally have a BET surface area of t to 50 m$^2$/g, a total pore volume of 0.1 to 1 ml/g and an average pore radius of 1 to 15×10$^{-8}$ m. Their bulk density is about 0.8 to 1.5 kg/l. Depending upon size and shape, the catalysts can be used in a fixed bed or in a fluidized bed as well.

The reaction of the methylpyridines, especially α-, β-, or γ-methylpyridines with ammonia and oxygen to the corresponding cyanopyridines takes place in a customary manner in the gaseous phase. Considerable latitude is allowed in this way for the selection of the reaction conditions. The reaction takes place mainly without the use of pressure or under a slight excess pressure up to approximately 3 bar at temperatures between 300° and 460° C. preferably between 320° and 440° C. It has proven to be advantageous to supply the required oxygen as air. It is advantageous, depending of the methylpyridine used, to mix in water vapor and/or nitrogen. The ratio of methylpyridine to ammonia, oxygen or air and, optionally, water vapor and/or nitrogen, can be selected within broad limits. It is in general advantageous to use about 2 to 10 moles, preferably 3 to 8 moles ammonia, about 20 to 40 moles, preferably 25 to 35 moles air, and about 0 to 20 moles, preferably 0 to 15 moles water vapor and/or nitrogen. About 1 t0 2 moles methylpyridine are advantageously fed into the reactor per hour per liter bulk volume of the catalyst.

In the examples "%" signifies percentages by weight if not otherwise designated.

The following are-used as concepts in the examples below:

$$\text{conversion} = \frac{\text{moles of hydrocarbon converted}}{\text{moles of hydrocarbon used}} \times 100(\%)$$

$$\text{Yield} = \frac{\text{moles of product produced}}{\text{moles of hydrocarbon used}} \times 100(\%)$$

$$\text{space-time yield} = \frac{\text{amount of nitrile produced/time}}{\text{bulk volume of the catalyst}} \left(\frac{g}{l \times h}\right)$$

$$\text{Selectivity} = \frac{\text{yield}}{\text{conversion}} \times 100\%$$

EXAMPLE 1

2.332 kg antimony trioxide, 469.9 g ammonium vanadate, 1.278 kg titanium dioxide (surface area 52 m$^2$/g), 1.162 kg montmorillonite tempered at 1040° C. with a BET surface area of 1 m$^2$/g, and 580.5 g silicon dioxide with a BET surface area of 200 m$^2$/g (Aerosil®) were suspended in 12.7 kg water. 506 g of a 10% potassium nitrate solution were added to this suspension under agitation. Then 2.14 kg 52% nitric acid were slowly added and the mixture heated to boiling temperature under reflux and maintained for 2 hours at boiling temperature. Immediately after the boiling phase a pH of 4.6 was adjusted with 25% aqueous ammonia solution and the mixture heated again for 2 hours under reflux. After this second boiling phase the batch was agitated overnight and then used directly for spray-drying. For this the batch was conducted to the spray dryer via a solids separator and dried at a throughput of air of approximately 50 m³/h, an inlet temperature of approximately 600° C. at a speed of 40,000 rpms. The powder obtained in this manner was separated on a cyclone and had a particle size of 2.2 to 2.4×10⁻⁵ m with a BET surface area of 100–120 m²/g. The catalytic powder obtained in this manner was intimately mixed with approximately 100 g pentaerythritol per 1000 g catalytic powder and then kneaded with 500 g of a 10% starch solution to a pasty mass.

The mass was extruded by a core-progressive discharge worm extruder through a nozzle with 4 bores 3 mm in diameter and cut with a wire into formed bodies approximately 5 mm long. The form bodies were pre-dried with air heated to approximately 60° C. and dried overnight in air. The air-dried formed bodies can then be used the next morning for tempering.

For tempering the specimens 80 g of the air-dried form bodies were filled into a tempering tube and maintained at the desired temperature for 60 min. After it cools off the catalyst is ready for use. Its composition corresponds to the formula $Si_{7.25}Ti_4V_1Sb_4K_{0.125}O_x$ (BET surface area 20 m²/g, total pore volume 0.35 ml/g, average pore radius 4–5×10⁻⁸ m).

EXAMPLE 2

A catalyst was produced in the same manner as described in example 1. However, twice the amount of potassium nitrate cited in example 1 was admixed to this catalyst. The method of spray-drying, formation and tempering remained unchanged. Its composition corresponds to the formula $Si_{7.25}Ti_4V_1Sb_4K_{0.25}O_x$ (BET surface area 25 m²/g, total pore volume 0.35 ml/g, average pore radius 4–6×10⁻⁸ m).

EXAMPLE 3

A catalyst was produced in the same manner as described in example 1. Four times the amount of potassium nitrate cited in example 1 was admixed to this catalyst. The method of spray-drying, formation and tempering remained unchanged. Its composition corresponds to the formula $Si_{2.75}Ti_4V_1Sb_4K_{0.5}O_x$ (BET surface area 30 m²/g total pore volume 0.35 ml/g, average pore radius 5–6×10⁻⁸ m).

EXAMPLE 4

A catalyst was produced in the same manner as described in example 1. 40% of the amount of potassium nitrate cited in example 1 was admixed to this catalyst. The method of spray-drying, formation and tempering remained unchanged. Its composition corresponds to the formula $Si_{2.75}Ti_4V_1Sb_4K_{0.05}O_x$ (BET surface area 20 m²/g, total pore volume 0.34 ml/g, average pore radius 5–6×10⁻⁸ m).

EXAMPLE 5

50 ml of a catalyst tempered according to example 1 and at 670° C. were filled into a reaction tube with an inner width of 20 mm and 500 mm in length. 75.4 mmoles 3-methylpyridine, 455.8 mmoles ammonia, 2250 mmoles air and 679 mmoles water vapor were fed hourly as a gaseous mixture into the tube. The reaction tube was heated by a salt bath which was maintained at 330°, 340° and 370° C. The catalyst was loaded with the gaseous mixture for 150 min at each temperature. Upon exiting from the reaction tube the gases were washed with water. The results of the catalytic tests are presented in Table 1:

TABLE 1

| temperature (°C.) | conversion (%) | yield (%) | selectivity (%) | space-time yield |
|---|---|---|---|---|
| 330 | 76.8 | 71.2 | 92.7 | 111.7 |
| 340 | 88.3 | 83.5 | 94.6 | 131.0 |
| 370 | 99.4 | 95.2 | 95.8 | 149.3 |

The conversion refers to the amount used; the yield of 3-cyanopyridine was related to the amount of 3-methylpyridine used. The space-time yield is indicated in grams per liter and hour.

EXAMPLE 6

The same method was used as in example 5; however, a catalyst produced according to example 2 was used which was tempered at 645° C. The charged amounts and temperatures are as described in example 5. The results of the catalytic tests are presented in Table 2:

TABLE 2

| temperature (°C.) | conversion (%) | yield (%) | selectivity (%) | space-time yield |
|---|---|---|---|---|
| 330 | 78.7 | 73.1 | 92.9 | 114.6 |
| 340 | 89.1 | 84.0 | 94.3 | 131.7 |
| 370 | 99.0 | 94.3 | 95.3 | 147.9 |

EXAMPLE 7

The same method was used as in example 5; however, a catalyst produced according to example 3 was used which was tempered at 645° C. The charged amounts and temperatures are as described in example 5. The results of the catalytic tests are presented in Table 3:

TABLE 3

| temperature (°C.) | conversion (%) | yield (%) | selectivity (%) | space-time yield |
|---|---|---|---|---|
| 330 | 69.5 | 65.7 | 94.5 | 103.0 |
| 340 | 81.7 | 77.8 | 95.2 | 122.0 |
| 370 | 97.4 | 93.0 | 95.2 | 145.9 |

EXAMPLE 8

The same method was used as in example 5; however, a catalyst produced according to example 4 was used which was tempered at 700° C. The charged amounts and temperatures are as described in example 5. The results of the catalytic tests are presented in Table 4:

TABLE 4

| temperature (°C.) | conversion (%) | yield (%) | selectivity (%) | space-time yield |
|---|---|---|---|---|
| 330 | 64.4 | 59.7 | 92.7 | 93.6 |
| 340 | 82.3 | 78.0 | 94.8 | 122.3 |
| 370 | 98.5 | 93.9 | 95.3 | 147.3 |

EXAMPLE 9

The same method was used as in example 5; however, instead of 3-methylpyridine, 2-methylpyridine was used and instead of water vapor an appropriate amount of nitrogen was used. The reaction gases were washed upon exiting from the reaction tube with N-methylpyrrolidone. The catalyst was tested, differently from example 5, that is only at 330°, 340° and 360° C. The results of the catalytic tests are presented in Table 5:

TABLE 5

| temperature (°C.) | conversion (%) | yield (%) | selectivity (%) | space-time yield |
| --- | --- | --- | --- | --- |
| 330 | 88.2 | 61.1 | 69.3 | 104.0 |
| 340 | 88.5 | 83.0 | 93.8 | 130.6 |
| 360 | 94.5 | 84.2 | 89.1 | 132.5 |

EXAMPLE 10

A catalyst was produced in the same manner as described in example 1. However, no potassium nitrate was admixed to this catalyst. The method of spray-drying, formation and tempering remained unchanged.

The method of example 5 was used and a catalyst used which had been tempered at 711° C. (BET surface area 20 m²/g). The results of the catalytic tests are presented in Table 6:

TABLE 6

| temperature (°C.) | conversion (%) | yield (%) | selectivity (%) | space-time yield |
| --- | --- | --- | --- | --- |
| 330 | 58.8 | 49.8 | 84.7 | 78.1 |
| 340 | 74.6 | 67.7 | 90.8 | 106.2 |
| 370 | 96.8 | 90.5 | 93.5 | 142.0 |

EXAMPLE 11

An estimation of the deactivation behavior of a catalyst doped with and without potassium was made in such a manner that the catalyst was tested in the lab on two days at different temperatures each day. A catalyst produced according to example 1 which had been tempered at 670° C. and one produced according to example 10 which had been tempered at 711° C. were used for the tests.

The tests took place as described in example 5; the results are presented in Table 7 with comparison of the yields achieved:

TABLE 7

| day | temperature | without potassium | with potassium |
| --- | --- | --- | --- |
| 1 | 330 | 65.7 | 74.7 |
| 2 | 330 | 49.8 | 74.7 |
| 1 | 340 | 80.6 | 85.5 |
| 2 | 340 | 67.7 | 85.0 |
| 2 | 370 | 90.5 | 94.3 |

Thus, the catalyst doped with potassium had higher yields of product than the catalyst not doped with potassium. It is expected that catalysts doped with other alkali metals would perform in a similar manner.

EXAMPLE 12

Stress tests were performed with the potassium-doped catalysts in order to achieve a greater space-time yield. To this end a catalyst produced according to example 1 and tempered at 670° C. was tested as described in example 5. However, in deviation from example 5, 100.5 mmoles 3-methylpyridine, 200 mmoles ammonia, 2100 mmoles air and 450 mmoles water vapor were fed in hourly as gaseous mixture. The results of the catalytic tests are presented in Table 8:

TABLE 8

| temperature (°C.) | conversion (%) | yield (%) | selectivity (%) | space-time yield |
| --- | --- | --- | --- | --- |
| 330 | 89.2 | 81.9 | 91.8 | 156.1 |

Further variations and modifications of the foregoing will be apparent to those skilled in the art and such variations and modifications are intended to be encompassed by the claims that are appended hereto.

German Priority Application 195 04 283.2 filed on 9 Feb. 1995 is relied on and incorporated by reference in its entirety.

We claim:

1. A catalyst for the reaction of methylpyridine with ammonia and oxygen to form the corresponding cyanopyridine, said catalyst represented by the formula (I)

$$Sb_a V_b Ti_c X^1_d X^2_e O_f$$

wherein $X^1$ is silicon obtained from highly dispersed silica and at least one layer-lattice silicate introduced during the production of said catalyst, $X^2$ is potassium, a=3–10, b=0.5–2, c=3–10, d=2–20, e=0.01–2, and f=atom number necessary for the stoichiometric saturation of the remaining components from the valencies and constituents.

2. The catalyst according to claim 1, wherein said catalyst has a BET surface area of 5 to 50 m²/g, a total pore volume of 0.1 to 1 ml/g and an average pore radius of 1 to 15×10⁻⁸ m.

3. The catalyst according to claim 1, wherein the atomic ratio of antimony:vanadium is between 2:1 and 20:1.

4. The catalyst according to claim 3, wherein the atomic ratio of antimony:vanadium is between 2:1 and 10:1.

5. The catalyst according to claim 1, wherein the atomic ratio of titanium:vanadium is between 2:1 and 8:1.

6. The catalyst according to claim 1, wherein said potassium is 0.01 to 15% measured on the atomic concentration of the total metal content of said catalyst excluding oxygen.

7. A method of producing a catalyst comprising the formula (I)

$$Sb_a V_b Ti_c X^1_d X^2_e O_f$$

wherein $X^1$ is silicon obtained from highly dispersed silica and at least one layer-lattice silicate introduced during the production of said catalyst, $X^2$ is potassium, a=3–10, b=0.5–2,
c=3–10,
d=2–20,
e=0.01–2, and
f=atom number necessary for the stoichiometric saturation of the remaining components from the valencies and constituents;

said method comprising mixing a compound of the elements antimony, vanadium, titanium and silicon with oxygen and potassium in the form of their oxygen compounds in a concentration corresponding to formula I with water, and optionally organic solvents miscible with water, to form an aqueous medium, wherein said silicon is obtained from highly dispersed silicon dioxide and layer-lattice silicate, wherein the atomic ratio of vanadium to titanium is less than 1 and the atomic ratio of antimony to vanadium is greater than 1 in the form of their oxygen compounds, wherein the amount of potassium is 0.01 to 15% measured on the atomic concentration of the total metal of the above-named elements excluding oxygen, with the proviso that the ratio of the potassium-metal atoms to the other above-named metals is less than 1 to 1 in each instance, adding nitric acid, boiling said aqueous medium at a first pH between 0 and 2 under reflux, adjusting said first pH to a second pH of 3 to 6, reboiling under reflux, and spray-drying to obtain a powder.

8. The method according to claim 7 further comprising adding extrusion aids, pore formers and solvents to said powder and kneading and extruding to obtain formed bodies.

9. The method according to claim 8 further comprising heating said form bodies at a temperature between 300° and 800° C. in the presence of oxygen.

10. The method according to claim 7, wherein said temperature is between 550° and 750° C.

11. The method according to claim 7, wherein said first pH is between 0.5 and 1.5.

12. The method according to claim 7, wherein said second pH is between 4 and 5.

13. The method according to claim 8, wherein said extrusion aids and pore formers are selected from the group consisting of ammonium carbonate, carbohydrates, polyvalent alcohols, and mixtures thereof.

14. The method according to claim 8, wherein said extrusion aids and pore formers are added in an amount of 1 to 30% by weight.

15. The method according to claim 8, wherein said extrusion aids and pore formers are added in an amount of 5 to 20% by weight.

16. The method according to claim 8, wherein said solvent is selected from the group consisting of water, organic solvents miscible with water, and mixtures thereof.

17. The method according to claim 14, wherein said organic solvents miscible with water are selected from the group consisting of mono-valent alcohol, polyvalent alcohol, and mixtures thereof.

18. The method according to claim 17, wherein said organic solvents miscible with water are selected from the group consisting of methanol, glycerol, glycol, and mixtures thereof.

19. The method according to claim 8, wherein the atomic ratio of titanium to vanadium in said catalyst is between 2:1 and 8:1.

20. The method according to claim 8, wherein the atomic ratio of antimony to vanadium in said catalyst is between 2:1 and 20:1.

21. The method according to claim 20, wherein the atomic ratio of antimony to vanadium in said catalyst is between 2:1 and 10:1.

22. The method according to claim 8, wherein said highly disperse silicon dioxide has a BET surface area of 50 to 500 $m^2/g$.

23. The method according to claim 22, wherein said highly disperse silicon dioxide has a BET surface area of 100 to 300 $m^2/g$.

24. The method according to claim 8, wherein said layer-lattice silicate is thermally pretreated by heating under constant movement to a temperature between 900° and 1200° C. for at least one hour but not longer than 10 hours.

25. The method according to claim 24, wherein said layer-lattice silicate is thermally pretreated by heating under constant movement to a temperature between 975° and 1100° C. for four hours to six hours.

26. The method according to claim 24, wherein said layer-lattice silicate is montmorillonite with a BET surface area of 0.1 to 10 $m^2/g$.

27. The method according to claim 8, wherein the weight ratio of said highly disperse silicon dioxide to said layer-lattice silicate is 1:1 to 1:10.

28. The method according to claim 27, wherein the weight ratio of said highly disperse silicon dioxide to said layer-lattice silicate is 1:1 to 1:5.

29. The method according to claim 8, wherein the atomic amount of silicon in all of said metals is 20 to 70%.

30. The method according to claim 29, wherein the atomic amount of silicon in all of said metals is 30 to 50%.

31. The method according to claim 8, wherein the ratio of said metals to said potassium is between 20:0.01 and 20:5.

32. The method according to claim 31, wherein the ratio of said metals to said potassium is between 20:0.1 and 20:3.

33. The method according to claim 8, comprising placing antimony or antimony trioxide under agitation into water and treating with nitric acid at boiling temperature and subsequently adding the other elements as nitrates or ammonium salts of their oxygen acids.

34. The method according to claim 8, comprising placing all elements in the form of their oxides, ammonium salts of their oxygen acids or nitrates under agitation in water and subsequently adding nitric acid.

* * * * *